(12) United States Patent
Chen et al.

(10) Patent No.: US 8,614,194 B1
(45) Date of Patent: Dec. 24, 2013

(54) ANIONIC CELL PENETRATING PEPTIDE AND ITS USE FOR INTRACELLULAR DELIVERY

(75) Inventors: Hui-Ting Chen, Kaohsiung (TW); Hsin-Fang Chang, Kaohsiung (TW); Yan-Hsiung Wang, Kaohsiung (TW); Chai-Lin Kao, Kaohsiung (TW)

(73) Assignee: Kaohsiung Medical University, Taipei (TW)

( * ) Notice: Subject to any disclaimer, the term of this patent is extended or adjusted under 35 U.S.C. 154(b) by 0 days.

(21) Appl. No.: 13/557,994

(22) Filed: Jul. 25, 2012

(51) Int. Cl.
*A61K 38/08* (2006.01)

(52) U.S. Cl.
USPC .......................................... 514/21.8; 514/1.2

(58) Field of Classification Search
None
See application file for complete search history.

(56) References Cited

U.S. PATENT DOCUMENTS 7,846,895 B2 * 12/2010 Eckert et al. .................... 514/2.6
2004/0110296 A1 * 6/2004 Vargeese et al. ............. 435/458

OTHER PUBLICATIONS

Sekido et al., Novel Drug Delivery System to Bone Using Acidic Oligopeptide: Pharmacokinetic Characteristics and Pharmacological Potential, Journal of Drug Targeting, vol. 9(2):111-121 (2001).*
Kasugai et al., Selective Drug Delivery System to Bone: Small Peptide (Asp)6 Conjugation; Journal of Bone and Mineral Research vol. 15(5):936-943 (2000).*
Blast Report of "AGDDAVS", HTTP://BLAST.NCBI.NLM.NIH.GOV, attached as pdf, available at http://blast.ncbi.nlm.nih.gov/Blast.cgi (keyword "AGDDAVS"), last visited Mar. 11, 2013.*

* cited by examiner

*Primary Examiner* — Cecilia J Tsang
*Assistant Examiner* — Randall L Beane
(74) *Attorney, Agent, or Firm* — Ditthavong Mori & Steiner, P.C.

(57) ABSTRACT

The disclosure provides a cell penetrating peptide. The cell penetrating peptide includes an amino acid sequence of $D_n$, in which D represents an aspartate residue and $2 \leq n \leq 15$.

12 Claims, 8 Drawing Sheets

ANIONIC CELL PENETRATING PEPTIDE AND ITS USE FOR INTRACELLULAR DELIVERY

FIELD OF THE INVENTION

The invention relates to a cell penetrating peptide, and more particularly, to an anionic cell penetrating peptide and its use for intracellular delivery.

BACKGROUND OF THE INVENTION

Cellular internalization of large hydrophobic therapeutic agents such as proteins or nucleic acids is still a challenging task because of the presence of a plasma membrane, which constitutes an impermeable barrier for these molecules. In order to circumvent this problem, several methods of carrier-mediated delivery systems have been developed. Among these methods, much attention has been focused on the use of peptide-based delivery systems. The use of peptides with cell penetrating properties has many advantages because of various modifications that can be done to the peptide sequence. This allows the engineering of carriers addressing different cellular subdomains and/or transporting various types of cargoes.

Some cell penetrating peptides (CPPs) are designed from the sequences of membrane-interacting proteins, like fusion proteins, signal peptides, transmembrane domains, and anti-microbial peptides. These sequences, also called protein transduction domains (PTDs), prove to cross biological membranes without a carrier or a receptor, and to deliver peptides or proteins into intracellular compartments. Many studies suggest that the use of PTD-based peptides is of major significance for therapies against viral diseases or cancers (Victoria Del Gaizo, R. Molecular Therapy 2003, 7, 720-730; Harada, H., et al. Cancer Research 2002, 62, 2013). Among the studies, the penetratin from the Drosophila antennapedia homeodomain protein (Derossi, D., et al. Journal of Biological Chemistry 1994, 269, 10444), and Tat peptide derived from the HIV-1 genome have been used to improve the cellular uptake of peptides, proteins, or oligonucleotides.

Some CPPs, designated as amphipathic peptides, have been described. An amphipathic molecule can be divided into two regions: a hydrophilic (polar) region and a hydrophobic (non-polar) region. For peptides, their amphipathic properties arise either from primary structure or from secondary structure. Primary amphipathic peptides are defined as the sequential assembly of a domain of hydrophilic residues with a domain of hydrophobic residues. Secondary amphipathic peptides are generated by the conformational state which allows the positioning of hydrophobic residues and hydrophilic residues on opposite sides.

Other CPPs, such as polyarginine-based peptides, are synthesized and employed as a tool for intracellular delivery of therapeutics. The cationic guanidine moiety on the side chain of polyarginine-based peptides plays a critical role in cell penetrating properties (Futaki, S. International Journal of Pharmaceutics 2002, 245, 1-7; Futaki, S., et al. Journal of Biological Chemistry 2001, 276, 5836). Rothbard et al. have substituted arginine residues systemically with neutral alanine residues, which results in a significantly reduced cellular uptake (Vives, E., et al. Letters in Peptide Science 1997, 4, 429-436). They also have replaced other positively charged amino acids such as lysine, ornithine, histidine, and citrulline with arginine residues, and similar outcome is gained. This implies that arginine possesses unique cell penetrating properties when comparing with other positively charged amino acids.

Studies up to today reveal that currently used CPPs are cationic and limited because of toxicity and the lack of efficiency. As such, the disclosure is to provide a new family of CPPs which are anionic and exhibit low toxicity and high efficiency.

SUMMARY OF THE INVENTION

One aspect of the disclosure is to disclose a cell penetrating peptide which comprises an amino acid sequence of $D_n$ and $2 \leq n \leq 15$.

Another aspect of the disclosure is to disclose a complex which comprises a cell penetrating peptide and a cargo. The cell penetrating peptide comprises an amino acid sequence of $D_n$ and $2 \leq n \leq 15$. The cargo is selected from the group consisting of a therapeutic agent, a diagnostic probe, a peptide, a nucleic acid, an antisense oligonucleotide, a protein, a nanoparticle, a liposome, a small molecule, and a radioactive material.

Still another aspect of the disclosure is to disclose a method for intracellular delivery. The method comprises the following steps: (a) providing a complex; and (b) incubating the complex with a targeted cell. The complex includes a cell penetrating peptide and a cargo. The cell penetrating peptide comprises an amino acid sequence of $D_n$ and $2 \leq n \leq 15$. The cargo is selected from the group consisting of a therapeutic agent, a diagnostic probe, a peptide, a nucleic acid, an antisense oligonucleotide, a protein, a nanoparticle, a liposome, a small molecule, and a radioactive material.

The detailed description and preferred embodiment of the disclosure will be set forth in the following content, and provided for people skilled in the art so as to understand the characteristic of the disclosure.

DETAILED DESCRIPTION OF THE INVENTION

The disclosure is based on a finding that a family of anionic peptides have cell penetrating properties and still have relatively high efficiency and low toxicity.

In the disclosure, a cell penetrating peptide is provided. The cell penetrating peptide has an amino acid sequence of $D_n$, in which D represents an aspartate residue and $2 \leq n \leq 15$, and preferably, $2 \leq n \leq 10$. In one embodiment, the cell penetrating peptide is selected as follows:

DD, (SEQ ID NO: 1)

DDDD, (SEQ ID NO: 2)

or

DDDDDD. (SEQ ID NO: 3)

The cell penetrating peptide further has a chemical entity which is covalently linked to the amino acid sequence. The chemical entity has a backbone of 3-12 atoms individually selected from a carbon atom or a nitrogen atom. The term "backbone" used in the content means the longest continuous chain directly bonded to the amino acid sequence. The chemical entity may be covalently linked to the N terminal of the amino acid sequence, to the C terminal of the amino acid sequence, or to both of the N terminal and the C terminal of the amino acid sequence. In one embodiment, the chemical entity is two alanine residues, four alanine residues, or one lysine residue covalently linked to the N terminal of the amino acid sequence. In another embodiment, the chemical entity is two lysine residues each covalently linked to the N terminal and the C terminal of the amino acid sequence. As a whole, the cell penetrating peptide may be selected as follows:

AADDDD, (SEQ ID NO: 4)

AAAADD, (SEQ ID NO: 5)

KDDDDDD, (SEQ ID NO: 6)

or

KDDDDDDK. (SEQ ID NO: 7)

Figure 1:
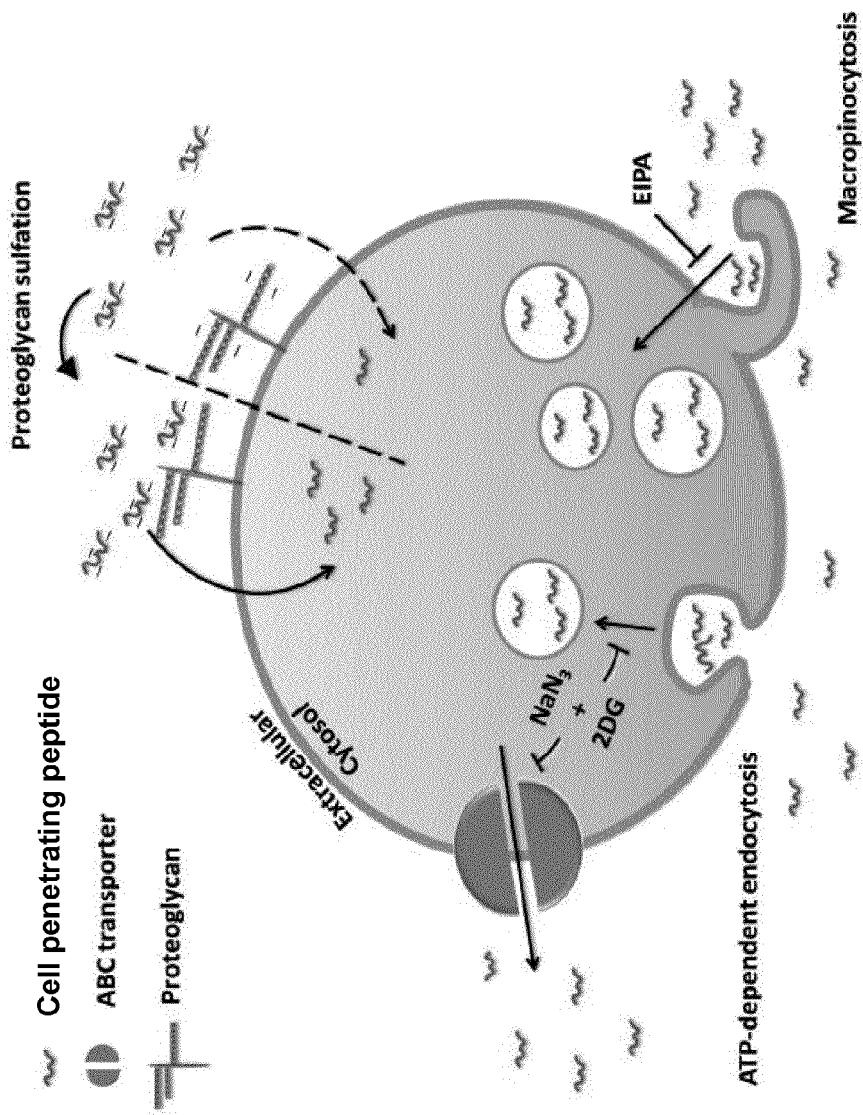
FIG. 1 is a schematic picture illustrating translocation into a cell and efflux from the cell of a cell penetrating peptide according to the invention.

With reference to FIG. 1, it is illustrated that the cell penetrating peptide can cross into a cell by: (1) direction translocation caused by proteoglycan sulfation; (2) macropinocytosis; and (3) ATP-dependent endocytosis. In such a way, the cell penetrating peptide delivers a cargo into the cell such as for medication use or for experiment use. The term "cargo" used in the content includes but not limited to a therapeutic agent, a diagnostic probe, a peptide, a nucleic acid, an antisense oligonucleotide, a protein, a nanoparticle, a liposome, a small molecule, or a radioactive material. With reference to FIG. 1 again, it is also illustrated that the cell penetrating peptide can cross out of the cell by an ABC (ATP-binding cassette) transporter. In such a way, the cell penetrating peptide delivers the cargo into the cell more efficiently by blocking an ABC transporter.

The disclosure further provides a complex. The complex has a cell penetrating peptide and a cargo, and both of them are as defined previously. In one embodiment, the cargo is γ-amino butyric acid (ABA), polyethylene glycol (PEG), fluorescein isothiocyanate (FITC), or cholesterol lowering drug simvastatin. Besides, the cargo may be covalently linked to the cell penetrating peptide, or form a stable complex with the cell penetrating peptide in a non-covalent manner.

The complex further has an ABC transporter blocker for blocking an ABC transporter. The ABC transporter blocker may be a chemical compound, such as but not limited to sodium azide ($NaN_3$), 2-deoxy-D-glucose (2-DG), sodium vanadate, or reserpine, or the ABC transporter blocker may be an antibody, such as but not limited to a monoclonal antibody, a polyclonal antibody, a human antibody, a humanized antibody, a diabody, a chimeric antibody, a multi-specific antibody, a heteroconjugate antibody, a single chain antibody, a domain antibody, or a modified configuration of an immunoglobulin molecule.

The disclosure still further provides a method for intracellular delivery. The method may be an experimental method, or a therapeutic method or a prevention method for a disease, and includes the following steps: (a) providing a complex as defined previously; and (b) incubating the complex with a targeted cell. Preferably, the targeted cell is but not limited to a skin cell, a bone cell, a lung cell, a neuron cell, a spleen cell, a kidney cell, a tumor cell, an ovary cell, or a stem cell. In one embodiment, the targeted cell is a HeLa cell or an adipose-derived stem cell (ADSC).

The following examples are provided for further description of the disclosure.

Example 1-1

Preparation of Complex ABA-KD$_6$

Rink amide resin (0.17 g, 0.1 mmol, load: 0.6 mmol/g) is swelled using dimethylformamide (DMF, 5 ml). Fmoc-amino acid and benzotriazol-1-yl-oxytripyrrolidinophosphonium hexafluorophosphate (PyBOP) are used at 0.4 mmol scale. Fmoc-Asp(tBu)-OH (0.4 mmol, 0.17 g) is coupled to the swelled resin following activation of PyBOP and 40% N-methylmorpholine in 3 ml DMF, and this coupling is repeated for five times. After activation of 20% piperidine in 5 ml DMF, Fmoc-Lys(ivDde)-OH is attached to the finally attached Fmoc-Asp(tBu)-OH. After deprotection of N terminal of the Fmoc-Lys(ivDde)-OH, ABA (0.4 mmol) is introduced to the Fmoc-Lys(ivDde)-OH. Finally, ivDde group is removed with reaction of 4% hydrazine, and then the remaining Fmoc-Lys(ivDde)-OH is capped by acetic anhydride or introduced with FITC. After resin cleavage using trifluoroacetic acid, the resulted solution is concentrated in vacuo. The residue is purified by an LH20 column using $CH_3OH$ as eluent, and therefore, complex ABA-KD$_6$ is provided. Yield: 13%. Purity: >95% (C5 column by HPLC system performed in isocratic solvent system of 0.1% TFA/MeOH under UV detection at 220 nm and 496 nm using 0.4 ml/min flow rate (retention time: 6.1 min)) Mass (MALDI-TOF): found for 1350 Da ([M+H]$^+$); calcd. for 1349 Da.

Example 1-2

Preparation of Complex KD$_6$K-Simvastatin

Wang resin (0.13 g, 0.1 mmol, load: 0.79 mmole/g) is swelled using DMF (5 ml). Fmoc-amino acid and PyBOP are used at 0.4 mmol scale. Fmoc-Lys(ivDde)-OH is attached to the swelled resin, and then Fmoc group of the Fmoc-Lys(ivDde)-OH is removed after activation with 20% piperidine in 5 ml DMF. A solution of simvastatin (0.4 mmol, 0.16 g) in 10% diisopropylethylamine/DMF is introduced to the remaining Fmoc-Lys(ivDde)-OH under microwave assistance (200 W, 105° C.). After activation of 4% hydrazine/DMF, Fmoc-Asp(tBu)-OH (0.4 mmol, 0.17 g) is coupled to the remaining Fmoc-Lys(ivDde)-OH, and this coupling is repeated for five times. After activation of 20% piperidine in 5 ml DMF, Fmoc-Lys(ivDde)-OH is attached to the finally attached Fmoc-Asp(tBu)-OH. After deprotection of N terminal of the newly added Fmoc-Lys(ivDde)-OH, $PEG_{500}$ (0.4 mmol, 0.23 g) is introduced to the remaining newly added Fmoc-Lys(ivDde)-OH. Finally, ivDde group of the remaining newly added Fmoc-Lys(ivDde)-OH is removed with reaction of 4% hydrazine, and then the remaining newly added Fmoc-Lys(ivDde)-OH is capped by acetic anhydride or introduced with FITC. After resin cleavage using trifluoroacetic acid, the resulted solution is concentrated in vacuo, and the residue is purified by an LH20 column using $CH_3OH$ as eluent. Therefore, complex $KD_6K$-Simvastatin is provided. Retention time: 8.2 min (in reverse-phase HPLC performed with C5 column under UV detection at 220 nm, using a flow rate of 0.2 mL/min and isocratic solvent system (0.1% TFA/MeOH)). Yield: 24%. Purity: >95%. Mass (MALDI-TOF): found for 2469 Da ([M−H]); calcd. for 2470 Da. $^1$H-NMR (solvent: D-acetone; 400 MHz): 8.49 (br, 1H), 7.93 (d, J=8 Hz, 1H), 7.16 (t, J=9 Hz, 2H), 6.71 (m, 9H), 4.73 (m, 4H), 4.36 (s, 2H), 4.22 (m, 4H), 3.36 (m, 40H), 3.29 (s, 3H), 2.87 (m, 12H), 1.84 (m, 12H), 1.54 (m, 8H), 1.4 (s, 3H), 1.3 (s, 6H), 1.21 (m, 4H), 0.88 (m, 2H).

Example 1-3

Preparation of Complex $PEG-KD_6$

This complex is prepared by a process similar to that as described in Example 1-1, except that $PEG_{500}$ (0.4 mmol, 0.23 g) is introduced to the Fmoc-Lys(ivDde)-OH after deprotection of N terminal of the Fmoc-Lys(ivDde)-OH. Retention time: 6.1 min. Yield: 17%. Mass (MALDI-TOF): found for 1846 Da ([$M+K+OCH_3-3H$]); calcd. for 1764 Da.

Example 1-4

Preparation of Complex Oleic Acid-$KD_6$

This complex is prepared by a process similar to that described in Example 1-1, except that oleic acid (0.6 mmol) is introduced to the Fmoc-Lys(ivDde)-OH after deprotection of N terminal of the Fmoc-Lys(ivDde)-OH.

Example 1-5

Preparation of Peptide $D_6$

This peptide is prepared using standard Fmoc-strategy with an Automatic Solid Phase Synthesizer. In detail, Fmoc-Asp(tBu)-OH (0.6 mmol, 0.274 g) is coupled following activation of PyBOP and 40% N-methylmorpholine in 3 ml DMF, and then this mixture is introduced into a vessel containing resin to react. Therefore, peptide $D_6$ is prepared. $^1$H NMR (300 MHz, $CD_3OD$) δ 4.638-4.740 (m, 6H), 2.866-3.085 (m, 12H); HPLC (Nucleodur-C18, MeOH: TFA 99.9: 0.1, 0.4 mL/min, k=220 nm) t=4.07 min Example 1-6

Preparation of Peptide $KD_6$

This peptide is prepared using standard Fmoc-strategy with an Automatic Solid Phase Synthesizer. In detail, Fmoc-Asp(tBu)-OH (0.6 mmol, 0.274 g) is coupled following activation of PyBOP and 40% N-methylmorpholine in 3 ml DMF, this mixture is introduced into a vessel containing resin to react, and then Fmoc-Lys(ivDde)-OH is added to the vessel to react again. Therefore, peptide $KD_6$ is provided.

Example 1-7

Preparation of Peptide $A_2D_4$

This peptide is prepared using standard Fmoc-strategy with an Automatic Solid Phase Synthesizer. In detail, Fmoc-Asp(tBu)-OH (0.6 mmol, 0.274 g) is coupled following activation of PyBOP and 40% N-methylmorpholine in 3 ml DMF, this mixture is introduced into a vessel containing resin to react, and then Fmoc-Ala(ivDde)-OH is added to the vessel to react again. Therefore, peptide $A_2D_4$ is provided. HPLC (Nucleodur-C18, 100% MeOH, 0.4 mL/min, k=220 nm) t=8.25 min.

Example 1-8

Preparation of Peptide $A_4D_2$

This peptide is prepared using standard Fmoc-strategy with an Automatic Solid Phase Synthesizer. In detail, Fmoc-Asp(tBu)-OH (0.6 mmol, 0.274 g) is coupled following activation of PyBOP and 40% N-methylmorpholine in 3 ml DMF, this mixture is introduced into a vessel containing resin to react, and then Fmoc-Ala(ivDde)-OH is added to the vessel to react again. Therefore, peptide $A_4D_2$ is provided. HPLC (Nucleodur-C18, 100% MeOH, 0.4 mL/min, k=220 nm) t=4.91 min.

Example 2

Cell Culture

Human adipose-derived stem cells (hADSCs) are purchased from Cellular Engineering Technologies (Coralville, Iowa) and grown in K-NAC medium (GIBCO-Invitrogen Corporation) supplemented with N-acetyl-L-cysteine (Sigma, 2 mM) and L-ascorbic acid 2-phosphate (Sigma, 0.2 mM). K-NAC medium contains 5% fetal bovine serum (FBS), 1% streptomycin-penicillin (GIBCO-Invitrogen Corporation) whereas growth factors and hormones for this medium are recombinant epidermal growth factor (rEGF, 5 ng/ml) and bovine pituitary extract (BPE, 25 μg/ml). HeLa cells are purchased from ATCC, and grown in Dulbecco's modified Eagle medium (DMEM) supplemented with 10% FBS. Medium are changed every other day and cells are incubated at 37° C. in an atmosphere of 5% $CO_2$ and 95% humidity.

Example 3

Cell Viability and Proliferation hADSCs or HeLa cells are seeded in a 96-well plate and grown to a density of $5 \times 10^3$ cells/well with medium. Cells are treated with test compound in concentration gradient from 1 μM to 1000 μM (30 μl/well) and incubated for 30 minutes or for 4 days at 37° C. After this treatment, PBS is added to each well. 20 μl, 1 of MTS reagent (Promega) is added to each well containing 200 μl, 1 of fresh medium, and incubated at 37° C. in 5% $CO_2$ for 3 hours. Then, the plate is read using ELISA reader (Bio-Rad) at 490 nm. Untreated cells as control group are treated with tris-buffer for 30 minutes instead of test compound. Viability is expressed as a part of 100% viability of control group.

Figure 2:
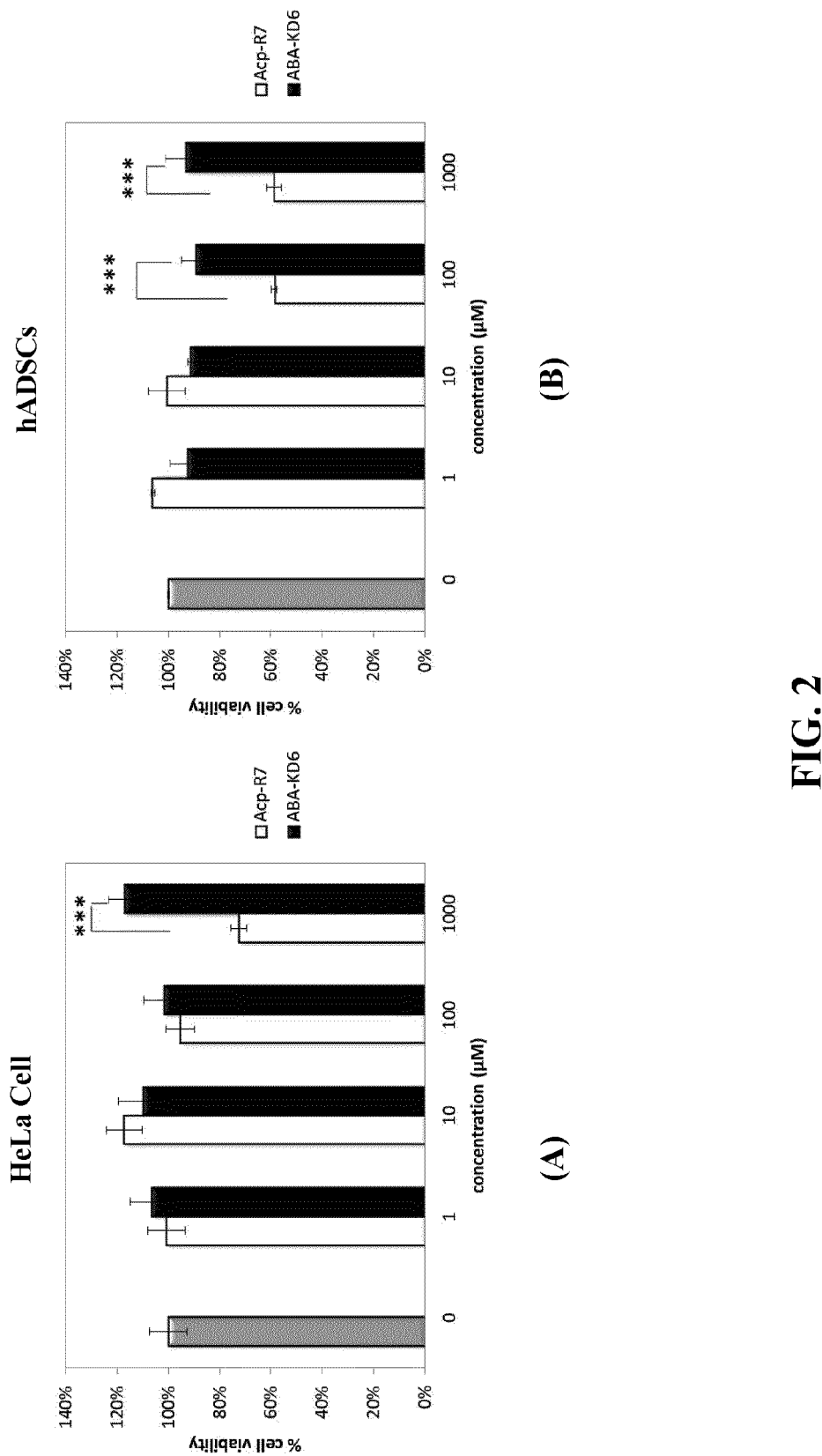
FIGS. 2(A) to 2(B) are bar charts respectively showing viability of HeLa cells and hADSCs treated with test compounds for 3 hours.
Figure 3:
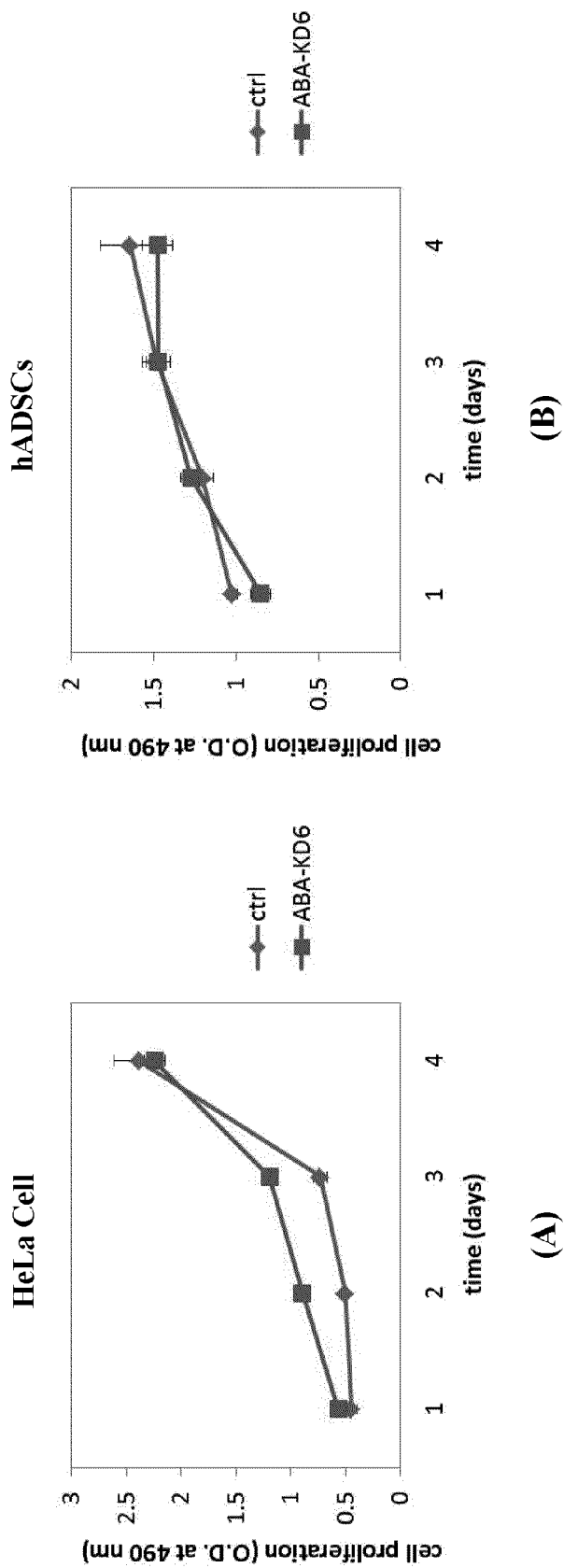
FIGS. 3(A) to 3(B) are diagrams respectively showing proliferation of HeLa cells and hADSCs treated with test compounds for 4 days.

As shown in FIGS. 2(A) to 2(B), it is found that cells treated with 100 μM or higher concentration of well known cationic penetrable complex 6-aminocaproic acid-$R_7$ (ACP-$R_7$, R: an arginine residue) present a relatively lower viability than those treated with the same concentration of ABA-$KD_6$. Please refer to FIGS. 3(A) to 3(B), which are diagrams respectively showing proliferation of HeLa cells and hADSCs treated with test compound for 4 days. It is learned that cells treated with 10 μM ABA-$KD_6$ maintain normal proliferation relative to untreated cells. As the foregoing results, complex ABA-$KD_6$ is proven to have no obvious toxicity for cells, especially in high concentration.

Example 4

Fluorescence Microscopy

Cells are treated with 10 μM test compound for 30 minutes at 37° C., washed using PBS, and then treated with 0.5% trypsin. Cells are labeled with 5 μg/ml Hoechst 33342 (Invitrogen) and PKH26-GL (Sigma) respectively for nuclei and membrane labeling. Standard protocols are followed according to the kit instructions. Cells are lastly suspended again in PBS for fluorescence images. Fluorescence images are captured by Olympus, CellR and Olympus FV1000 confocal microscope using glass-bottom culture slides with excitation by 488 nm (FITC-labeled peptide) laser line.

Figure 4:
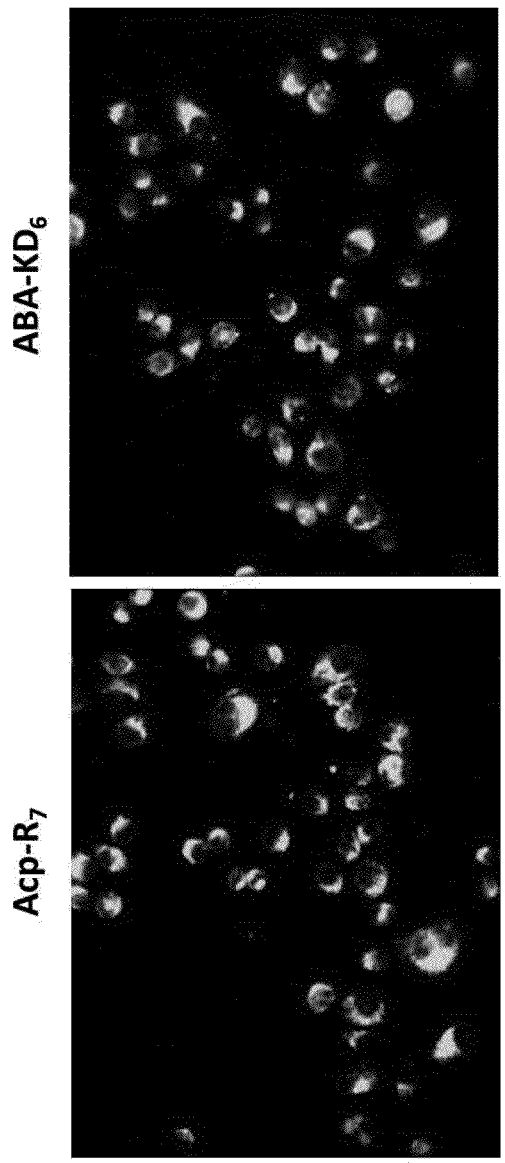
FIG. 4 is a picture showing that test compounds translocate into HeLa cells.
Figure 5:
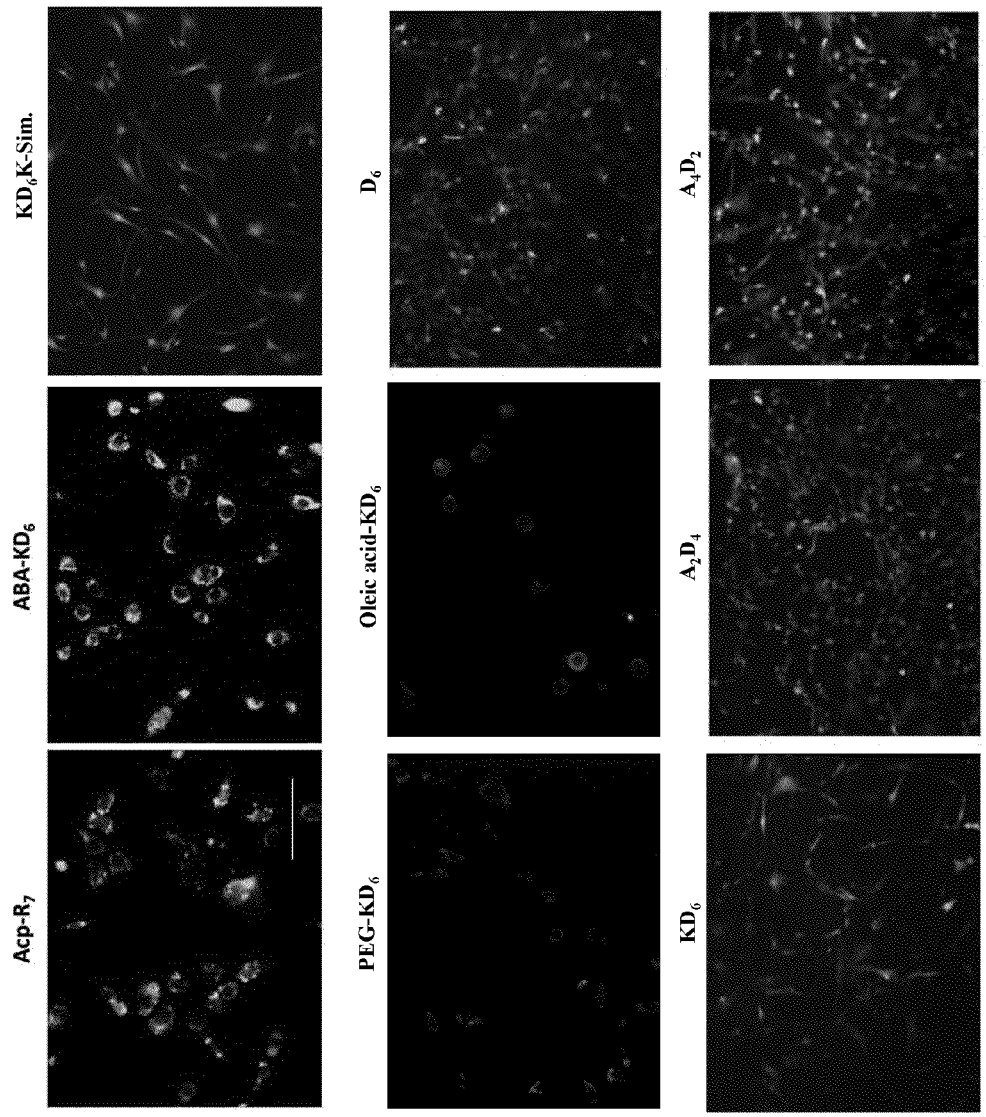
FIG. 5 is a picture showing that test compounds translocate into hADSCs.

As shown in FIG. 4, FITC-labeled complex ACP-$R_7$ crosses into HeLa cells, and so does FITC-labeled ABA-$KD_6$. As shown in FIG. 5, well known penetrable FITC-labeled complex ACP-$R_7$ crosses into ADSCs, and so do FITC-labeled ABA-$KD_6$, $KD_6$K-simvastatin, PEG-$KD_6$, oleic acid-$KD_6$, $D_6$, $KD_6$, $A_2D_4$, and $A_4D_2$.

Example 5

Flow Cytometry

FACSArray is used to analyze internalization of test compound. $2\times10^5$ hADSCs or HeLa cells are collected in a microtube after centrifugation. Suspension cells are treated with 10 μM test compound (200 μl), and then either incubated at 37° C. for 30 or 60 minutes, or incubated at 4° C. for 30 or 60 minutes. The cells are treated with 0.5% trypsin (200 μl) at 37° C. for 5 minutes, and then 200 μl of culture medium is added to the cells. The cells are precipitated by centrifugation at 1200 rpm for 5 minutes. After removing supernatant, the precipitated cells are washed with 1 ml of PBS and collected by centrifugation at 1200 rpm for 5 minutes. Notably, keep all reagents at 4° C. After this washing, the cells are suspended in PBS (200 μl) and subjected 10000 events to fluorescence analysis on a FACSarray (BD Biosciences) flow cytometer using a 488 nm laser excitation and a 515-545 nm emission filter. The analysis and presentation of the data are done using the WinMIDI software package (http://facs.scripps.edu/software.html).

Figure 6:
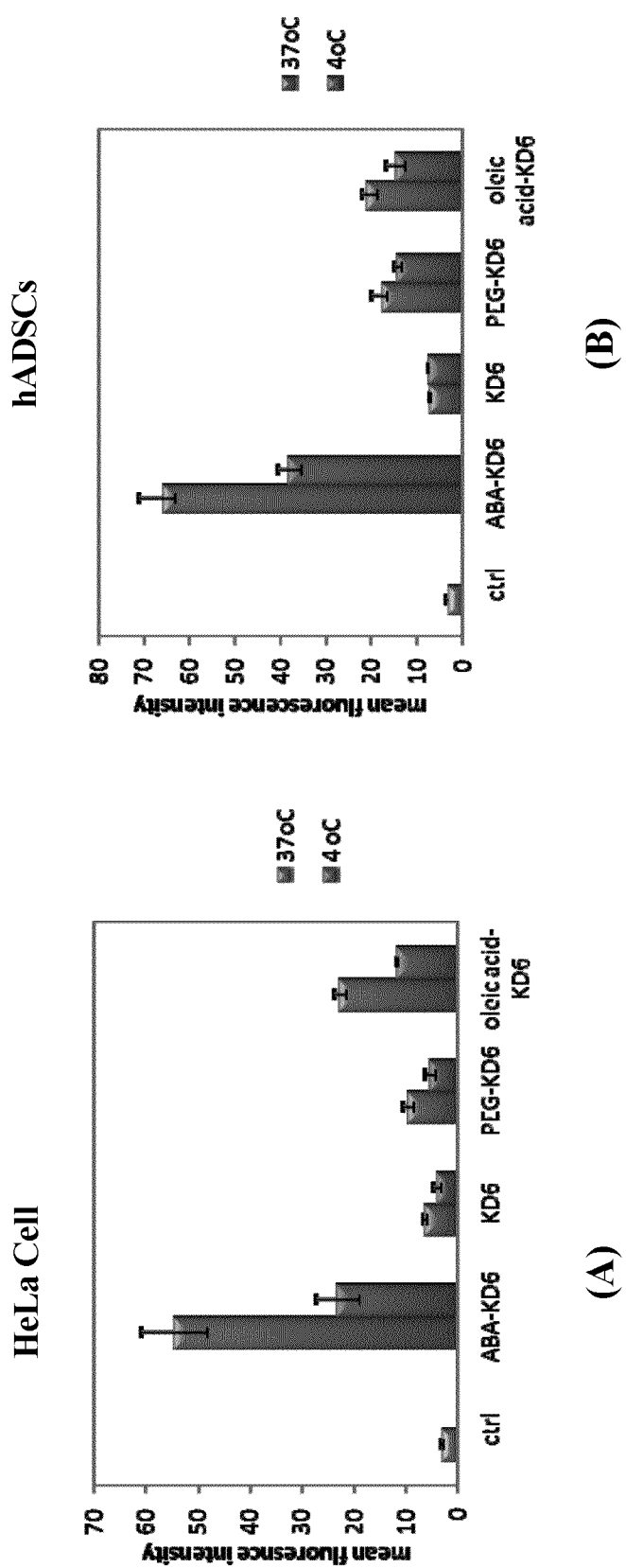
FIGS. 6(A) to 6(B) are bar charts respectively showing uptake of HeLa cells and hADSCs treated with test compounds for 30 minutes.

As shown in FIGS. 6(A) to 6(B), it is found that cells treated with 10 μM ABA-$KD_6$ either at 37° C. or at 4° C. present a excellent fluorescence intensity, which implies ABA-$KD_6$ may cross into cells in an non-energy-dependent manner. Secondly, it is found that cells treated with 10 μM ABA-$KD_6$ at 37° C. have a relatively higher fluorescence intensity than those at 4° C., and this implies that ABA-$KD_6$ may cross into cells in an energy-dependent manner.

Figure 7:
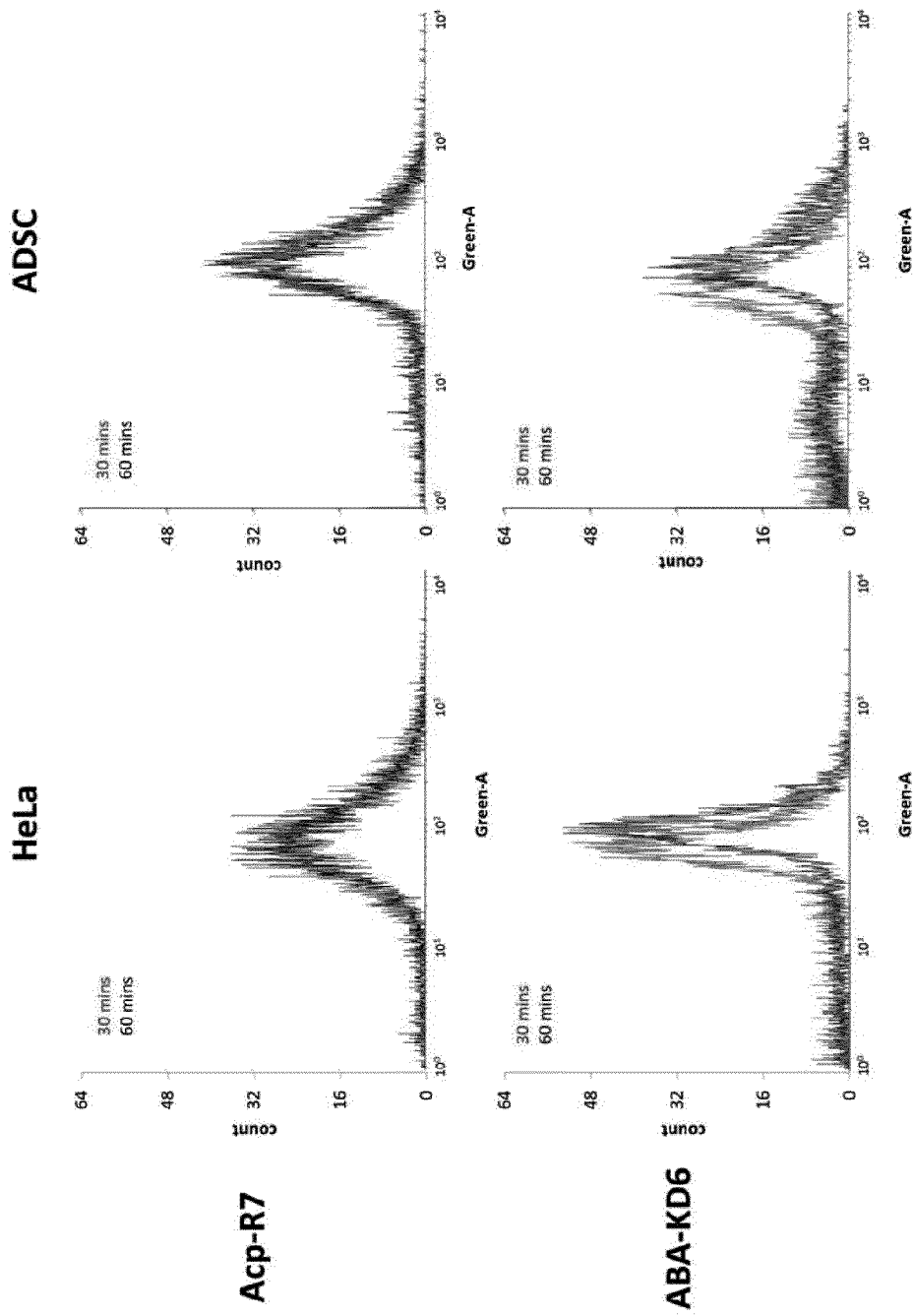
FIG. 7 is a diagram showing uptake of HeLa cells and hADSCs treated with test compounds for 30 or 60 minutes.

As shown in FIG. 7, it is surprising that hADSCs treated with 10 μM ABA-$KD_6$ at 37° C. for 60 min present two peaks of fluorescence, and this suggests that ABA-$KD_6$ may efflux from cells after crossing into the cells for a period.

Example 6

Endocytosis Inhibition Analysis

For inhibition of endocytosis, HeLa cells are treated with 200 mM sodium azide ($NaN_3$; Sigma) and 2-deoxy-D-glucose (2DG; Sigma) for 1 hour to deplete intracellular ATP pools and influence cell metabolism. hADSCs are treated with 10 mM $NaN_3$ and 2DG for 1 h with the same purpose. For inhibition of macropinosome formation, HeLa cells and hADSCs are treated with 3 mM 5-(N-ethyl-N-isopropyl) amiloride (EIPA, Sigma) for 10 minutes. For inhibition of proteoglycan sulfation, HeLa cells and hADSCs are treated with 600 mM sodium chlorate ($NaClO_3$, Sigma) for 2 days. After this treatment of inhibitors, cells are treated with 10 μM test compound (200 μl), and then incubated at 37° C. for 30 minutes. $10^4$ cells in 0.1 ml medium are seeded into each well of a 24-well plate, and then trypsin (200 μl) is added into each well. Cells are transferred to a microtube and incubated for 5 minutes. Cells are processed for flow cytometry as described above after being added with 200 μl of medium and washed with PBS.

Figure 8:
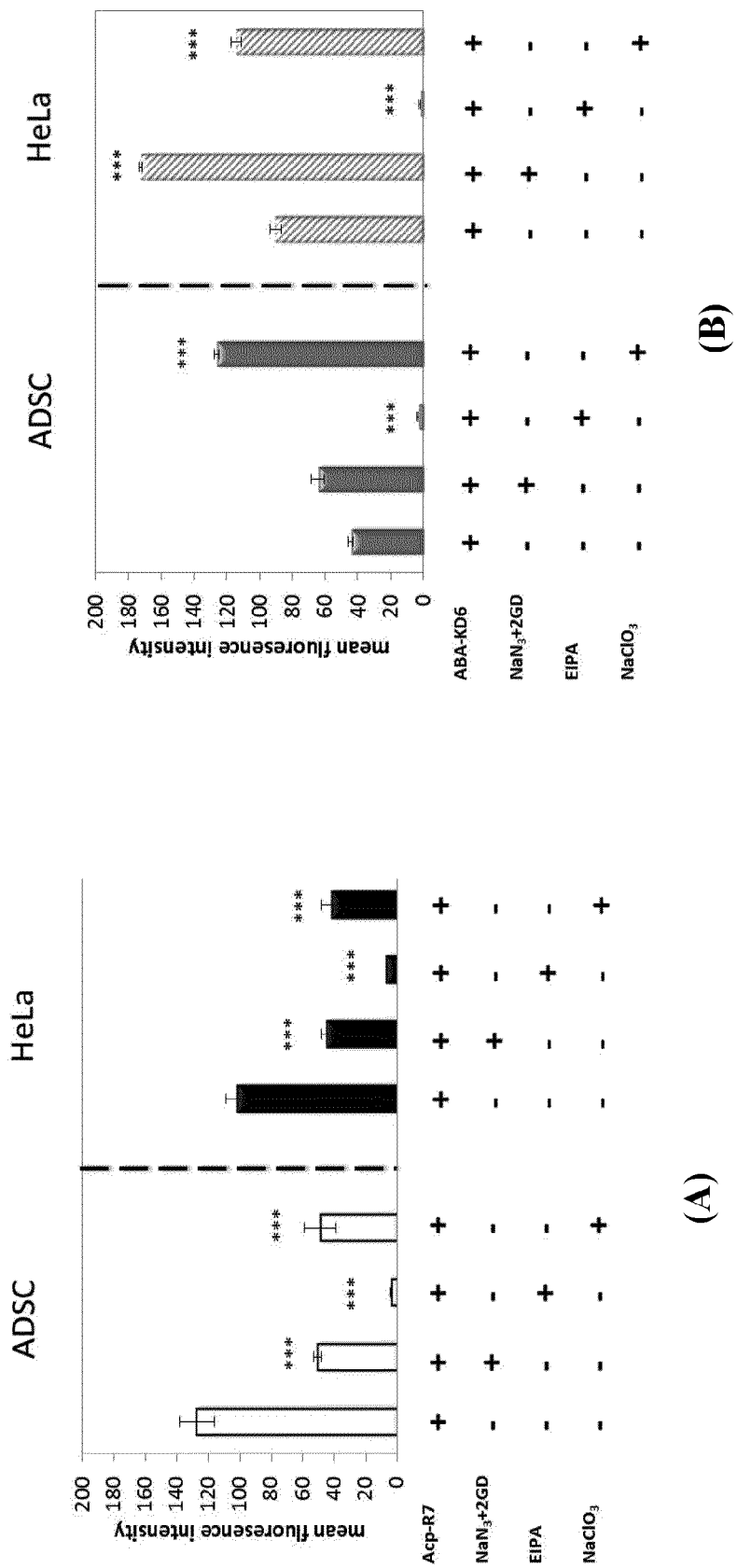
FIGS. 8(A) to 8(B) are bar charts respectively showing uptake of HeLa cells and hADSCs treated with test compounds combined with inhibitors.

Please refer to FIGS. 8(A) to 8(B), which are bar charts respectively showing uptake of HeLa cells and hADSCs treated with test compound combined with inhibitors. It is well known that Acp-$R_7$ is internalized by macropinocytosis, endocytosis, and direct translocation resulted from proteoglycan sulfation, and this phenomenon has reproduced as shown in FIG. 8(A). As shown in FIG. 8(B), cells treated with ABA-$KD_6$ combined with EIPA present a dose-dependent inhibition for uptake, and this indicates ABA-$KD_6$ is internalized by macropinocytosis. It is surprising that cells treated with ABA-$KD_6$ combined with $NaN_3$ and 2DG present a dose-dependent manner for uptake, and this phenomenon may be resulted from that ABA-$KD_6$ effluxes by ATP-involved pathway, such as ABC transporter. Moreover, it is surprising that cells treated with ABA-$KD_6$ combined with $NaClO_3$ also present a dose-dependent manner for uptake, which may be resulted from that the electrostatic repulsion on cellular surface for anionic molecule is reduced with $NaClO_3$.

Example 7

Statistical Analysis

All data values in the foregoing examples are presented as mean values (±SD) of at least six independent experiments. Data are analyzed by the Student's t test, and statistical significance is assumed of a p value of less than 0.05.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

Sequence Listing
<160> NUMBER OF SEQ ID NOS: 7
<210> SEQ ID NO: 1
<211> LENGTH: 2
<212> TYPE: PRT
<213> ORGANISM: Artificial
<220> FEATURE:
<223> OTHER INFORMATION: Synthetic Peptide
<400> SEQUENCE: 1
Asp Asp
1
<210> SEQ ID NO: 2
<211> LENGTH: 4
<212> TYPE: PRT
<213> ORGANISM: Artificial
<220> FEATURE:
<223> OTHER INFORMATION: Synthetic Peptide
<400> SEQUENCE: 2
Asp Asp Asp Asp
1
<210> SEQ ID NO: 3
<211> LENGTH: 6
<212> TYPE: PRT
<213> ORGANISM: Artificial
<220> FEATURE:
<223> OTHER INFORMATION: Synthetic Peptide
<400> SEQUENCE: 3
Asp Asp Asp Asp Asp Asp
1               5
<210> SEQ ID NO: 4
<211> LENGTH: 6
<212> TYPE: PRT
<213> ORGANISM: Artificial
<220> FEATURE:
<223> OTHER INFORMATION: Synthetic Peptide
<400> SEQUENCE: 4
Ala Ala Asp Asp Asp Asp
1               5
<210> SEQ ID NO: 5
<211> LENGTH: 6
<212> TYPE: PRT
<213> ORGANISM: Artificial
<220> FEATURE:
<223> OTHER INFORMATION: Synthetic Peptide
<400> SEQUENCE: 5
Ala Ala Ala Ala Asp Asp
1               5
<210> SEQ ID NO: 6
<211> LENGTH: 7
<212> TYPE: PRT
<213> ORGANISM: Artificial
<220> FEATURE:
<223> OTHER INFORMATION: Synthetic Peptide
<400> SEQUENCE: 6
Lys Asp Asp Asp Asp Asp
1               5
<210> SEQ ID NO: 7
<211> LENGTH: 8
<212> TYPE: PRT
<213> ORGANISM: Artificial
<220> FEATURE:
<223> OTHER INFORMATION: Synthetic Peptide
<400> SEQUENCE: 7
Lys Asp Asp Asp Asp Asp Asp Lys

```
                        SEQUENCE LISTING

<160> NUMBER OF SEQ ID NOS: 7

<210> SEQ ID NO 1
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 1

Asp Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Asp Asp Asp Asp
1

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 3

Asp Asp Asp Asp Asp Asp
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Ala Ala Asp Asp Asp Asp
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Ala Ala Ala Ala Asp Asp
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Lys Asp Asp Asp Asp Asp Asp
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Lys Asp Asp Asp Asp Asp Asp Lys
1               5
```

What is claimed is:

1. A synthesized cell penetrating peptide, consisting of:
a sequence of KDDDDDD (SEQ ID NO: 6), wherein K indicates a lysine residue and D indicates an aspartate residue.

2. A complex, comprising:
a synthesized cell penetrating peptide as claimed in claim 1; and
a cargo selected from the group consisting of a diagnostic probe, a peptide, a nucleic acid, a protein, a nanoparticle, a liposome, a small molecule, and a radioactive material.

3. The complex as claimed in claim 2, wherein the cargo is covalently linked to the synthesized cell penetrating peptide.

4. The complex as claimed in claim 3, wherein the cargo is covalently linked to the N-terminal end of the synthesized cell penetrating peptide's sequence.

5. The complex as claimed in claim 2, wherein the cargo forms a stable complex with the synthesized cell penetrating peptide in a non-covalent manner.

6. The complex as claimed in claim 2, further comprising:
an ABC transporter blocker.

7. A method for cellular delivery, comprising:
administering a complex as claimed in claim 2 to a targeted cell.

8. The method as claimed in claim 7, wherein the cargo is covalently linked to the synthesized cell penetrating peptide.

9. The method as claimed in claim 8, wherein the cargo is covalently linked to the N-terminal end of the synthesized cell penetrating peptide's sequence.

10. The method as claimed in claim 7, wherein the cargo forms a stable complex with the synthesized cell penetrating peptide in a non-covalent manner.

11. The method as claimed in claim 7, wherein the complex further comprises:
an ABC transporter blocker.

12. The method as claimed in claim 7, wherein the targeted cell is selected from a group consisting of a skin cell, a bone cell, a lung cell, a neuron cell, a spleen cell, a kidney cell, a tumor cell, an ovary cell, and a stem cell.

* * * * *